United States Patent [19]

Hammond, III

[11] 4,381,154

[45] Apr. 26, 1983

[54] METHOD OF AND APPARATUS FOR NONDESTRUCTIVELY DETERMINING THE COMPOSITION OF AN UNKNOWN MATERIAL SAMPLE

[75] Inventor: Ogden H. Hammond, III, Winchester, Mass.

[73] Assignee: The Hetra Corporation, Newport, R.I.

[21] Appl. No.: 191,087

[22] Filed: Sep. 26, 1980

[51] Int. Cl.³ .............................................. G01N 25/00
[52] U.S. Cl. ..................................................... 374/43
[58] Field of Search ................ 73/15 R, 15 A, 190 R; 374/43

[56] References Cited

U.S. PATENT DOCUMENTS

| | | | |
|---|---|---|---|
| 3,266,307 | 8/1966 | Winter | 73/190 |
| 3,279,239 | 10/1966 | Arends et al. | 73/15 |
| 3,765,237 | 10/1973 | Blackener | 73/190 |
| 3,789,654 | 2/1974 | Jones | 73/15 |
| 3,892,125 | 7/1975 | Nunogaki | 73/15 |
| 3,981,175 | 5/1975 | Hammond et al. | 73/15 |
| 4,088,447 | 5/1978 | Walker | 73/190 |

OTHER PUBLICATIONS

Stansbury et al. "Adiabatic Calorimeter for Metals in the Range 50°-1000° C." in Review of Scientific Insts. Feb. 1959, pp. 121-126.

Primary Examiner—Herbert Goldstein

[57] ABSTRACT

The composition of a sample is determined with reference to a recorded standard using the same heater and sensor as that used to record the standard, by testing the sample only when its temperature has reached an equilibrium, and by compensating for differences in environment and starting temperature; accurate heater control is insured by maintaining a constant voltage across a series circuit consisting of a heater and a resistance load equal to the resistance of the heater; the heater is pulsed in an initial test sequence to heat the system to above ambient so that heat losses to the environment are substantially the same from test to test; a dynamic insulation system prevents heat loss from the sample under test; an improved test based on the sensed temperature of the sample immediately after the heater is turned off detects the presence of tungsten forgeries; a compensated infrared sensor eliminates the need for a direct contact temperature sensor; and tests are provided for determining various physical characteristics of an unknown sample.

23 Claims, 9 Drawing Figures

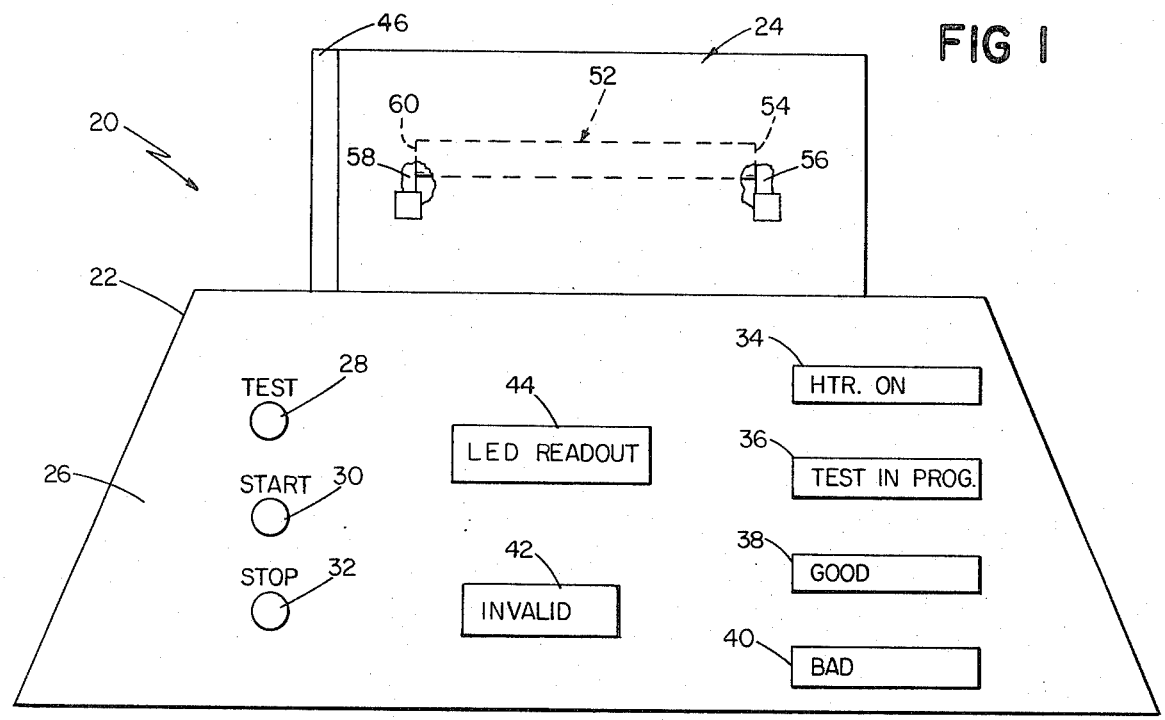

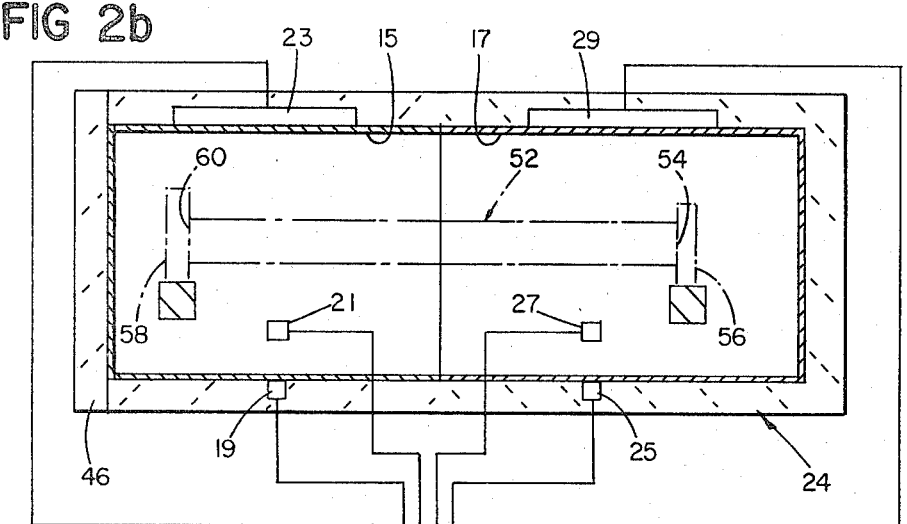
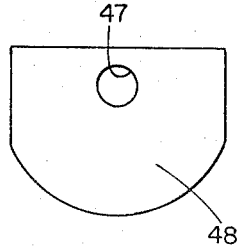
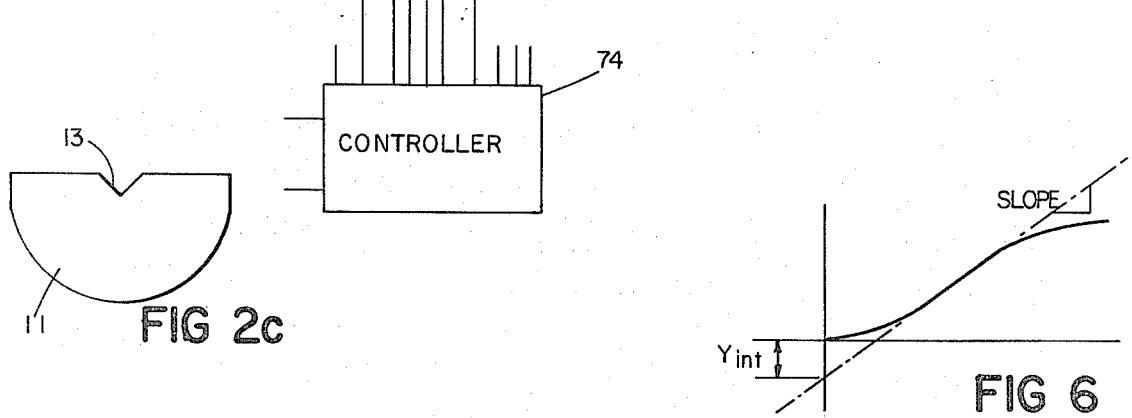
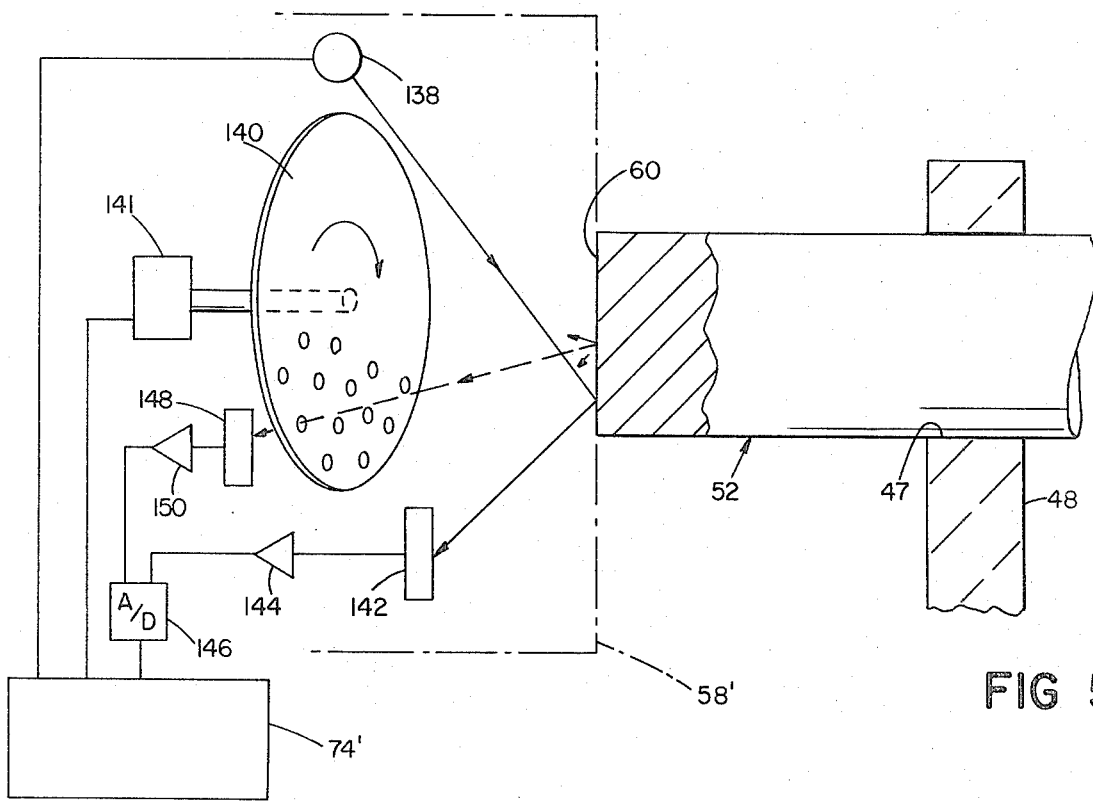

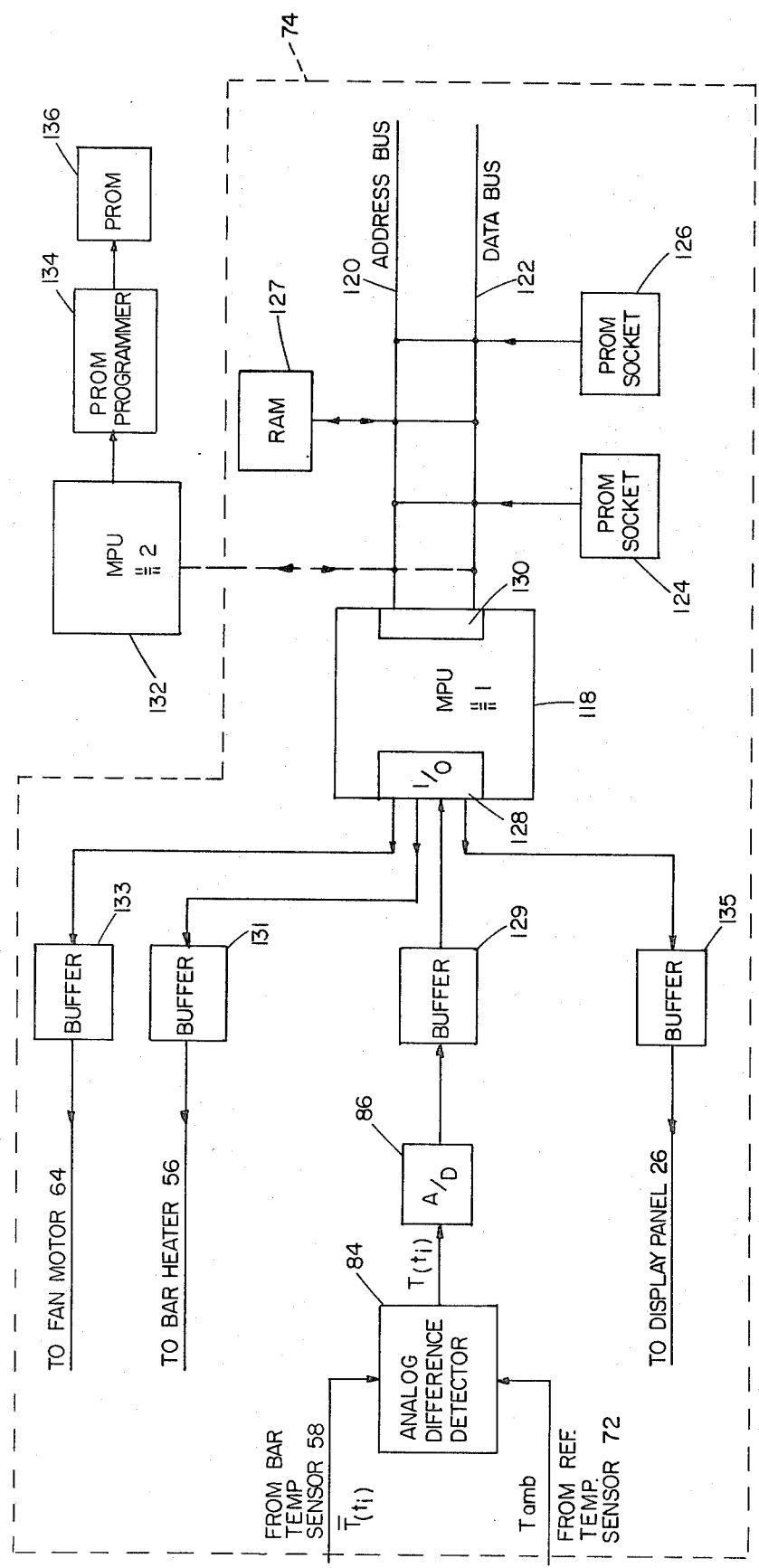

METHOD OF AND APPARATUS FOR NONDESTRUCTIVELY DETERMINING THE COMPOSITION OF AN UNKNOWN MATERIAL SAMPLE

BACKGROUND OF THE INVENTION

This invention relates to determining, by nondestructive test methods, the purity of composition of bars of material of a given shape; and more particularly, to determining whether a bar of precious metal has a purity of composition which is within a given range of variance from that of a standard bar of known purity of composition.

U.S. Pat. No. 3,981,175, issued Sept. 21, 1976 (hereby expressly incorporated by reference), discloses an apparatus for making such a nondestructive determination, wherein a standard bar, of known purity of composition, and a sample bar, whose purity of composition is desired, are both placed in a thermal chamber. A heat pulse of finite duration is applied to one end of both bars and the temperature vs. time responses of the opposite ends of both bars are monitored to determine the similarity of response. The patent recognizes, also, the possibility of sequential testing, in which the time vs. temperature response of a sample bar is compared with the previously stored time vs. temperature response of a standard bar.

The principal objects of the present invention are to provide an improved system for making such a comparison between the temperature response of a sample bar and the temperature response of a stored standard, and improved systems which may not use such a stored standard, wherein the measurements of temperature responses are improved by better control of heat losses, uniformity of temperature ranges, establishment of conditions of heat equilibrium, and better methods of temperature detection by the elimination of contact resistances.

Other objects of the present invention are improved systems for detecting tungsten forgeries and for determining the density, thermal conductivity, and heat capacity of a given material.

SUMMARY OF THE INVENTION

According to the present invention, the composition of a sample is determined with reference to a recorded standard using the same heater and sensor as that used to record the standard, by testing the sample only when its temperature has reached an equilibrium, and by compensating for differences in environment and starting temperature. In systems which may or may not include a recorded reference standard, accurate heater control is insured by maintaining a constant voltage across a series circuit consisting of a heater and a resistance load equal to the resistance of the heater; the heater is pulsed in an initial test sequence to heat the system to above ambient so that heat losses to the environment are substantially the same from test to test; a dynamic insulation system prevents heat loss from the sample under test; an improved test based on the sensed temperature of the sample immediately after the heater is turned off detects the presence of tungsten forgeries; a compensated infrared sensor eliminates the need for a direct contact temperature sensor; and tests are provided for determining various physical characteristics of an unknown sample.

Preferred embodiments, of course, may include any desired number of the above and other features.

DESCRIPTION OF THE EMBODIMENTS

We turn now to a description of the embodiments, after first briefly describing the drawings.

FIG. 1 is an elevation of a gold authentification device embodying the invention, for determining the purity of composition of a material.

FIG. 2 is a block diagram of the authentification device of FIG. 1.

FIG. 2(a) is an elevation of a rod support used in the authentification device.

FIG. 2(b) is a sectional view of an alternate embodiment of the chamber of FIG. 2.

FIG. 2(c) is an elevation of an alternate rod support used in the authentification device.

FIG. 4 is a block diagram of another embodiment of the control circuit of the authentification device of FIG. 1.

FIG. 5 is a block diagram of an alternative embodiment of a temperature sensor used in the authentification device of FIG. 1.

FIG. 6 is a temperature vs. time response of a bar of general composition.

Figure 3:
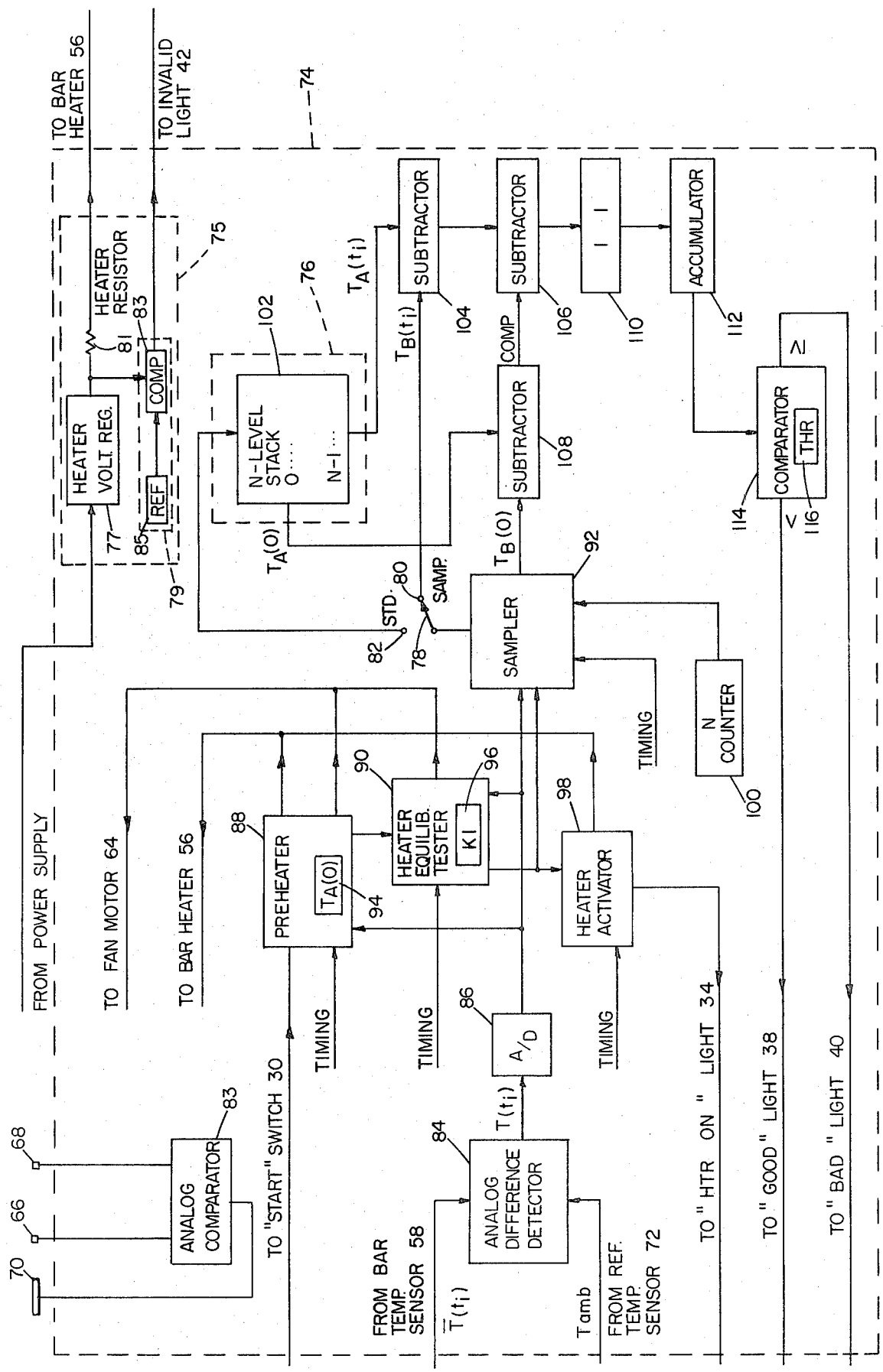
FIG. 3 is a schematic of the control circuit of the authentification device of FIG. 1.

Referring now to FIG. 1, gold authentification device 20 is generally made up of a base 22 and a test chamber 24 mounted on base 22. Base 22 is provided with a front panel display 26, upon which are mounted a "test" switch 28, a "start" switch 30, a "stop" switch 32, a "heater on" lamp indicator 34, a "test in progress" indicator lamp 36, a "good" indicator lamp 38, a "bad" indicator lamp 40, and an "invalid" indicator lamp 42. Additionally, display 26 has a three digit 7 segment LED digital display 44.

Chamber 24 is provided with a displacable end 46 through which the interior of chamber 24 may be accessed. End 46 may be attached to chamber 24 by hinges or held in place by clamps, etc.

Referring now to FIG. 2, chamber 24 is further provided with stepped supports 48 which are attached alternately, to the top and bottom interior walls of chamber 24, and which, as shown more particularly in FIG. 2(a), are provided with a hole 47 through which the bar may pass. Holes 47, being machined to accommodate bars of only the proper size, provide an immediate check as to whether the bar is of the proper diameter. This is important, since bars of different diameters will exhibit different temperature responses, even if of the same composition.

Referring now to FIG. 2(c), an alternate bar support 11 is provided with a notch 13 for positioning the bar. Supports 11 are utilized in an embodiment of authentification device 20 for testing the responses of bars having a square or rectangular cross section. In such an embodiment, supports 11 are attached to the top and bottom interior walls of chamber 24 in the stepped fashion shown in FIG. 2.

With end 46 displaced, either a standard bar 50, of known purity of composition, or a sample bar 52, whose purity of composition is to be compared to that of bar 50, may be inserted into chamber 24, so as to be contacted and supported by supports 48 (or supports 11 if square or rectangular bars are being used). If of the proper size and correctly positioned within chamber 24, one end 54 of the bar will come into contact with a bar heater 56 provided within chamber 24. A bar temperature sensor 58, also provided within chamber 24, is positioned so as to contact the other end 60 of the bar. End 46 is now replaced, making chamber 24 a suitable thermal chamber in which to test the thermal conductivity of the bar by applying, through the action of heater 56, a short but intense heat pulse to end 54 and measuring, through the action of sensor 58, the heat response with respect to time, of end 60.

Heater 56 and sensor 58 apply heat and sense temperature while in surface contact with ends 54 and 60, respectively. Supports 48 are constructed of a material having a low thermal conductivity and heat capacity. As a result, little heat flow takes place between the bar and the walls of chamber 24.

A fan 62, mounted within chamber 24, and an associated driving motor 64 are also provided. Fan 62 is positioned over an air inlet 59 in the bottom wall of chamber 24. An air outlet 61, also in the bottom wall of chamber 24, is provided at the opposite end of chamber 24. When fan 62 is activated, air, from outside chamber 24, is drawn in through inlet 59, to pass over the bar and other surfaces interior of chamber 24 and exit through outlet 61. This forced air convection within chamber 24 establishes thermal equalibrium between all surfaces interior to chamber 24. For example, if chamber 24 had an elevated temperature due to repeated testing and, if a sample bar, not having such as elevated temperature, was placed in chamber 24, the activation of fan 62 would soon bring the bar and the interior of chamber 24 to a common intermediate temperature. However, due to the fact that heat rises, in the absence of forced convection by fan 62, heat does not flow from chamber 24 though inlet 59 or outlet 61. Additionally, the configuration provided by supports 48 minimizes heat flow due to natural convection. Thus, when heater 56 is activated with fan 62 in an off state, a very high percentage of heat flow to sensor 58 will take place through the bar, and very little heat will flow from heater 56 to sensor 58 by natural air convection.

The specific arrangement of fan 62, inlet 59 and outlet 61 forms no part of the invention claimed herein, but is a specific embodiment of another invention of the inventor and the subject of another patent application, now being prepared.

A second temperature sensor 66 is also provided within chamber 24. Sensor 66 is positioned within chamber 24 so as to sense its average internal temperature and, therefore, should be positioned somewhat intermediate of heater 56 and sensor 58.

A third temperature sensor 68 is mounted on the exterior wall of chamber 24 to sense the average external surface temperature of chamber 24. Further, a conventional contact heater 70 is provided, mounted on the exterior surface of chamber 24, thus enabling the heating of the exterior surface of chamber 24.

The provision of sensor 66, sensor 68 and heater 70 allows an effective means of reducing heat losses from chamber 24, since heater 70 can be activated whenever the temperature of the exterior of chamber 24, as indicated by sensor 68, is lower than the interior temperature of chamber 24, as indicated by sensor 66.

Referring now to FIG. 2(b) chamber 24 may alternatively be constructed of an outer shell 13 and an inner shell composed of a number of segments, not connected, but only in abutting juxtaposition at their boundaries. The inner shell is shown in FIG. 2(b) as being composed of segments 15 and 17. However, the number of segments is by no means restricted to two.

In a similar manner as explained above for sensors 66 and 68 and heater 70, sensors 19 and 21 and heater 23 serve to minimize heat loss through segment 15, while sensors 25 and 27 and heater 29 reduce the heat loss through segment 17. In other words controller 74 is able to independently alter heaters 23 and 29 respectively, in response to temperature differentials sensed by sensor pairs 19 and 21, in the first case, and 25 and 27, in the second case. Since the end of chamber 24 containing bar heater 56 will have an elevated temperature compared to the end of chamber 24 containing sensor 58, such segmented dynamic insulation serves even further to reduce heat loss from chamber 24 to the ambient environment.

Referring now to FIG. 2, a fourth temperature sensor 72 is positioned at a location generally remote from, and, to the extent possible, not affected by any heat propagation from chamber 24, but in contact with the general ambient environment of authentification device 20, to provide a reference temperature. In practice locating the sensor has posed a difficult problem, and it has been found necessary to place it within base 22 of FIG. 1 to satisfy the necessary heat and temperature requirements.

All of the above active elements (i.e., heater 56, sensor 58, motor 64, sensor 66, sensor 68, heater 70, and sensor 72) are electrically connected to a controller 74, described in more detail below. A nonvolatile storage bank 76, which will not lose information stored within it when the power supplied to it is terminated, is provided within controller 74 which may, as described below, either store or retrieve binary data from storage bank 76.

A sampler 92 and a bipolar switch 78, having a "sample" terminal 80 and a "standard" terminal 82, are also provided within controller 74.

Generally, authentification device 20 functions as follows.

At all times when authentification device 20 is operating (e.g., for instance, whenever power is being supplied to it), controller 74 compares the temperatures of sensors 66 and 68. If the temperature of sensor 66 is greater than that of sensor 68, controller 74 activates heater 70, thus raising the temperature of the exterior surface of chamber 24. This process serves to minimize heat loss from chamber 24, due to the lack of a substantial temperature gradient. Therefore, the thermal conductivity of either bar 50 or bar 52 may be more accurately measured.

To store the temperature vs. time response of standard bar 50 to a fixed heat pulse, bar 50 is positioned in chamber 24 with its ends 54 and 60 in contact with heater 56 and sensor 58. End 46 is sealed and switch 78 is moved to contact terminal 82.

With fan 62 activated, the interior temperature of chamber 24 and the temperature of bar 50 are now raised to an elevated temperature, herein designated as $T_A(O)$. When sample bars are later tested they are also raised to a temperature in the vicinity of $T_A(O)$ by pulsing bar heater 56. This insures that standard bars and sample bars are tested under conditions in which the heat losses from chamber 24 are similar. Since, during repeated testings of sample bars, chamber 24 will grow warm and heat losses will increase, it is preferable to measure the temperature vs. time response of both standard and sample bars at temperatures higher than chamber 24 would normally have when first activated.

With standard bar 50 at $T_A(O)$ and fan 62 activated, controller 74 now samples the temperature of sensor 58 at discrete intervals of time, compares the absolute difference between each sample temperature and the earlier sample temperature to a constant, K1, stored internally, and deactivates fan 62 only when K1 is not exceeded by the absolute difference. After a short delay, controller 74 again samples the temperature of sensor 58 at successive instants of time, again compares the absolute difference between each sample temperature and the earlier sample temperature with K1, and activates bar heater 56 whenever the absolute difference falls below K1. In this manner, a desired degree of thermal equilibrium is established within chamber 24 and in bar 50.

Controller 74 now activates bar heater 56, causing it to deliver a short but intense pulse of heat to bar 50, and samples the temperature of sensor 58 at set and equal intervals of time, $\Delta t$. N samples of the temperature of sensor 58, $T_A(t_i)$, for $i=0,1,2,\ldots N-1$, are placed in storage 76, with heater 56 being deactivated after N/3 samples have been taken.

To compare the purity of composition of sample bar 52 with that of standard bar 50, sample bar 52 is placed in chamber 24 in the same manner as described above for standard bar 50, and switch 78 is moved so as to contact terminal 80. The temperature of sensor 58, and thus the temperature of sample bar 52, is compared, by controller 74, to the first temperature response sample of standard bar 50 (i.e., $T_A(O)$), stored in storage 76. Fan 62 is activated and heater 56 is then pulsed, if necessary, until the temperature of sensor 58 equals $T_A(O)$.

In the same manner as above described, fan 62 remains activated until the absolute difference between successive temperature samples from sensor 58 falls below K1, at which point controller 74 deactivates fan 62. Continued successive samples of the temperature of sensor 58 are taken, and, when the absolute difference between successive samples falls below K1, controller 74, in the same manner as described above, activates bar heater 56, so as to deliver to bar 52 the same short but intense heat pulse as was applied to bar 50, and takes N samples of the temperature of bar sensor 58, with bar heater 56 being deactivated after N/3 sample are taken. The N samples of the temperatures of bar sensor 58, herein designated $T_B(t_i)$, for $i=0,1,2\ldots N-1$, are taken at the same relative instants of time following activation of bar heater 56 as were samples $T_A(t_i)$.

Controller 74 finds the absolute difference between each corresponding pair of samples (i.e., $|T_A(t_i)-T_B(t_i)|$) and accumulates these absolute differences to yield a figure of merit given by $$\sum_{o}^{N-1} |T_A(t_i) - T_B(t_i)|.$$

Controller 74 compares this figure of merit with a threshold value, THR, stored internally, and activates "bad" light 40 if $$\sum_{o}^{N-1} |T_A(t_i) - T_B(t_i)| \geq THR.$$

Control circuit 74 activates "good" light 38 if the above condition is not fulfilled.

Certain refinements are possible in measuring the temperature vs. time response of either bar 50 or bar 52. For example, although the above described procedure serves to insure that the absolute difference between $T_B(O)$ and $T_A(O)$ is not great, in actual practice $T_B(O)$ will not equal $T_A(O)$. To compensate for this, it has been found desirable to construct controller 74 so that it will subtract a compensation factor, given by $T_A(O)-T_B(O)$, from each absolute temperature response difference, $|T_A(t_i)-T_B(t_i)|$. The resulting figure of merit, when controller 74 is thus constructed, is given by $$\sum_{o}^{N-1} |T_A(t_i) - T_B(t_i) - Comp|,$$

where $Comp=T_A(O)-T_B(O)$.

Further, since the ambient temperature of the environment of authentification device 20 will always influence, to some degree, the temperature vs. time response of either bar 50 or bar 52, it has been found desirable to construct controller 74 so that only the differences between the temperature responses of either bar 50 or bar 52 and the temperature of reference sensor 72, $T_{amb}$, are considered. When controller 74 is so constructed, $T_A(t_i)$ and $T_B(t_i)$ are given by $T_A(t_i)=\overline{T}_A(t_i)-T_{amb}$ and $T_B(t_i)=\overline{T}_B(t_i)-T_{amb}$, where $\overline{T}_A(t_i)$ and $\overline{T}_B(t_i)$ are the actual temperature samples of sensor 58 for standard bar 50 and sample bar 52, respectively. Temperature samples $T_A(t_i)$, $T_B(t_i)$, $T_A(O)$, and $T_B(O)$ are then acted on by controller 74 in the manner described above.

Referring now to FIG. 3, controller 74 is provided with an analog comparator 83, having as inputs, analog signals from sensors 66 and 68. Whenever the signals from sensors 66 and 68 indicate that the temperature of sensor 66 is greater than the temperature of sensor 68, comparator 83 activates heater 70, thus creating the "dynamic insulation" explained above.

Alternatively, comparator 83 may have inputs from sensors 19, 21, 25 and 27 of FIG. 2(b) and may activate heaters 23 and 29, also shown there, to create segmented dynamic insulation.

It is important that the amount of heat delivered by heater 56 be the same for the standard bar run and all sample bar runs. Since heater 56 is activated for the same period of time during all runs this condition will be met if the power consumption of heater 56 is kept constant throughout its activation interval. To this end, is provided heater power control circuit 75, consisting of heater voltage regulator 77, heater resistor 81, and heater voltage monitor 79, in turn consisting of voltage comparator 83 and voltage reference 85.

Regulator 77 insures that the voltage existing across the series circuit of resistor 81 and heater 56 remains at a constant value. The voltage level maintained by regulator 77 is dependent on the properties of heater 56 and the temperature range in which it is desired that it be operative. In practice, it has been found desirable that heater 56 reach a temperature of approximately 600° F. in its active state.

The electrical resistance of most materials is dependent on their temperature. This is typically true of the types of commercially available heater elements which might be employed to serve as heater 56. If a constant voltage, such as that supplied by regulator 77, was used to excite heater 56, the power consumed by heater 56 would vary according to $E^2/\Delta R$, where R is the change in resistance of heater 56. Provision of resistor 81, having a resistance approximately equal to the resistance of heater 56 over its operative range, serves to minimize fluctuations in the power consumption of heater 56, resulting in a more constant rate of heat flow from heater 56 to the bar.

Comparator 83 compares the voltage supplied by regulator 77 to the resistor and heater circuit to a desired voltage level supplied by reference 85. If the two voltages are not within a desired range of each other, comparator 83 activates invalid light 42 to indicate the unreliability of the run.

Controller 74 is also provided with an analog difference detector 84, having input signals from bar sensor 58 and reference sensor 72. Analog detector 84, provides, to an analog-to-digital converter 86, an analog signal given by $T(t_i) = \overline{T}(t_i) - T_{amb}$, where $T(t_i)$ is the reference compensated temperature of bar sensor 58, $\overline{T}(t_i)$ is the actual temperature of bar sensor 58, and $T_{amb}$ is the temperature of reference sensor 72.

Converter 86 provides digital signals, representative of $T(t_i)$ to a digital preheater 88, a digital heat equilibrium tester 90, and a digital sampler 92.

When enabled by start switch 30, preheater 88, as explained above, compares the reference compensated temperature of bar sensor 58 to a predetermined starting temperature, $T_A(O)$, stored in a register 94. If the reference compensated temperature of bar sensor 58 is less than $T_A(O)$, preheater 88 activates fan 62 and pulses bar heater 56. When the reference compensated temperature of bar sensor 58 is equal to $T_A(O)$, preheater 88 provides an enabling signal to heat equilibrium tester 90.

Tester 90, as explained above, compares the reference compensated temperature of bar sensor 58 at successive instants of time, and, when such temperatures vary by less than a value K1, stored in a register 96, deactivates fan 62. Tester 90 then continues to compare the reference compensated temperatures of bar sensor 58 at successive instants of time and, when such temperatures vary by less than K1, provides an enabling signal to a heater activator 98, and to sampler 92.

Heater activator 98, responsive to a time input, activates bar heater 56 for a period of time given by $N/3 \times \Delta t$, where N is the number of temperature samples taken by sampler 92 and t is the same interval between successive samples. At the same time it activates bar heater 56, heater activator 96 also activates "heater on" light 34.

Sampler 92, responsive to an N counter 100 and a timing input, takes N consecutive samples of the reference compensated temperature of bar sensor 58. If switch 78 is in contact with terminal 82, as when the standard response is being stored, the N samples are stored in an N-level stack register 102, located within storage 76 of FIG. 2.

If switch 78 is in contact with terminal 80, as when a sample bar is being tested, each reference compensated temperature sample, $T_B(t_i)$, is provided as input to a subtractor 104. Subtractor 104 also has an input, successive standard reference compensated temperature samples, $T_A(t_i)$, from stack register 102. The output of subtractor 104, given by $T_A(t_i) - T_B(t_i)$, is provided as input to a subtractor 106.

When a sample bar is being tested, the first reference compensated temperature response sample $T_B(O)$ is sent, by sampler 92, to a subtractor 108, which is also provided as input, $T_A(O)$, from stack register 102. Subtractor 108 provides, as input to a subtractor 106, the compensation factor, given by Comp = $T_A(O) - T_B(O)$. The output of subtractor 106, given by $T_B(t_i) - T_A(t_i) -$ Comp, is provided as input to an absolute value circuit 110, which, in turn, provides to an accumulator 112, the absolute value given by $|T_B(t_i) - T_A(t_i) - \text{Comp}|$.

Accumulator 112 accumulates N of these values over a sample run and then provides the accumulated absolute differences to a comparator 114. If the accumulated absolute differences, $$\sum_{0}^{N-1} |T_B(t_i) - T_A(t_i) - \text{Comp}|,$$

exceeds or is equal to a value THR, stored in a register 116, comparator 114 activates "bad" light 40, on display panel 26. Otherwise, comparator 114 activates "good" light 38, on display panel 26.

It will be seen that the functions carried out by controller 74 may be implemented either by hard wired circuitry, as above described, or by microprocessor circuitry. In practice, it has been found to be commercially desirable to employ microprocessor circuitry.

Referring now to FIG. 4, showing a preferred commercial embodiment of controller 74, microprocessor 118 (i.e., the National Semiconductor SC/MP) has an address bus 120 and a data bus 122. PROM sockets 124 and 126, compatible to mate with commercially available programmable read only memories, are connected to both buses 122 and 120. Additionally, a random access memory (i.e., RAM) 127, is also be connected to buses 120 and 122. Microprocessor 118 also has an input/output port (i.e., I/O port) 128, through which it is able to receive signals from a buffer 129 representative of the reference compensated temperature of bar sensor 58. Additional buffers 131 and 133 are also provided, through which microprocessor 118 may send activating signals to bar heater 56 and fan 62, respectively. Thus, by addressing any one of buffers 129, 131, or 133, microprocessor 118 may determine the reference compensated temperature of bar sensor 58 and activate or deactivate either bar heater 56 or fan 62. Still another buffer 135 allows microprocessor 118 to activate any of the lights on display panel 26 and to determine the condition of the various switches there. Microprocessor 118 is further provided with a disable switch 130, which, when activated, removes microprocessor 118 from busses 120 and 122.

A second microprocessor 132, having associated memories and peripherals which are not shown, is connectable to busses 120 and 122 via jumper cables. Microprocessor 132 is connected to a programmable read only memory programmer 134.

In the process of manufacturing authentification device 20, it has been found advantageous to employ the following procedure.

Standard bar 50 is placed in chamber 24. A PROM containing a program to perform the above described steps for storing the temperature vs. time response of standard bar 50 (i.e., heating standard bar 50 to a reference compensated temperature $T_A(O)$, ensuring the establishment of a relative degree of heat equilibrium, applying a heat pulse to standard bar 50, and determining the reference compensated temperature response of bar sensor 58 at N successive time instants) is inserted in socket 124.

This program is then run, and the N temperature responses of standard bar 50 are stored in RAM 127.

Microprocessor 132 is then connected to buses 120 and 122 and switch 130 is used to disable microprocessor 118. Microprocessor 132 is programmed to access the standard bar temperature responses stored in RAM 127 and pass them to a PROM programmer 134, which "burns" them in a PROM unit 136 which is compatible with socket 126.

Microprocessor 132 is then disconnected from buses 120 and 122, switch 130 is used to enable microprocessor 118, and PROM unit 136 is plugged into socket 126.

The PROM containing the program to store the standard temperature responses is removed from socket 124 and replaced with a second PROM, which supplies an instruction program to microprocessor 118 in accordance with the above described sequences for testing a sample bar 52. Thus, the sample PROM in socket 124 will instruct microprocessor 118 to heat sample bar 52 to a temperature near $T_A(O)$, establish heat equilibrium within chamber 24 and in bar 52, pulse bar heater 56, take N reference compensated temperature responses, and use the standard temperature responses $T_A(t_i)$ stored in the PROM in socket 126 to calculate $$\sum_{o}^{N-1} | T_A(t_i) - T_B(t_i) - Comp |.$$

Based on the accumulated absolute differences, microprocessor 118 will activate either "good" light 38 or "bad" light 40.

Alternatively, the above described program to store the temperature vs. time response of standard bar 50, as well as the above described program to test a sample bar 52 may both be placed in a ROM unit. The program in ROM may be constructed to store the temperature responses if a "standard" flag is raised and compute the figure of merit if it is not.

Referring now to FIG. 5, alternate bar sensor 58', which does not require contact with end 60 of either bar 50 or bar 52, has an infrared light source 138 which is flashed at a rate controlled by controller 74'. A chopping disc 140 is rotated by a motor 141, the angular rotation of which is also determined by output from controller 74'. Prior to sampling the temperature response of either bar 50 or bar 52, light source 138 is flashed for a short interval of time, while chopping disc 140 is held motionless. Light from source 138 is reflected from end 60 of either bar 50 or bar 52 to strike a detector 142, the amount of light striking detector being a function of, and thus indicative of, the reflectivity of end 60. Responsive to the degree of infrared light striking it, detector 142 provides a signal to amplifier 144. The amplified signal is then digitally quantitized by an analog-to-digital converter 146 and sent to controller 74'.

Thereafter, light source 138 is kept in an off state while chopping disc 140 is rotated. The amount of energy which is radiated by end 60 and passes through chopping disc 140 to strike a detector 148 is function of the emissivity, and thus the temperature, of end 60, and is also a function of the reflectivity (since reflectivity = 1 − emissivity) of end 60. Detector 148 emits a signal which is amplified by an amplifier 150 and digitally quantitized by converter 146 before being sent to controller 74'.

Controller 74', being thus provided with a signal representative of the reflectivity of end 60 and a signal which is a function of the reflectivity and emissivity of end 60, is able to derive the emissivity, and thus the temperature, of end 60.

Alternatively, the relative degree of rotation of chopping disc 140 may be controlled so that chopping disc 140 rotates out of phase with light source 138. Thus, whenever flashing light source 138 is in an on state, reflected light from end 60 is prevented from passing through a hole in chopping disc 140. In this embodiment, measurements of emissivity and reflectivity may be interleaved in time.

Forgeries of precious metals divide into two categories: alloyed forgeries, wherein the composition of the forgery is generally uniform throughout, and non-alloyed forgeries, wherein a discrete mass of a less precious metal is embedded within a larger mass of the precious metal sought to be imitated. Of all possible forgeries, a non-alloyed tungsten forgery of gold is the most difficult to detect, due to the fact that the density and heat-capacity of tungsten and gold are virtually identical.

I have discovered that, if a non-alloyed tungsten forgery is placed in chamber 24 and subjected to the same short but intense heat pulse as other sample bars, the most significant difference in the temperature vs. time responses of an unadulterated standard bar and a non-alloyed tungsten forgery occurs a very short period of time after the heat pulse has been terminated (i.e., typically less than 1 second), the temperature response of the non-alloyed tungsten forgery being greater than that of standard bar 50.

Using either the microprocessor control circuit of FIG. 4 or a hard wired equivalent circuit, it is possible to employ authentification device 20 to detect non-alloyed tungsten forgeries. The standard procedure described above is followed. However, an additional figure of merit is obtained, given by:

$$\frac{T_A(t_{off} + \Delta) - Comp}{T_B(t_{off} + \Delta)}$$

where $t_{off}$ is the time at which bar heater 56 is deactivated and $\Delta$ is a time interval on the order of 500 msec.

If the microprocessor control circuit 74 of FIG. 4 is employed, the reference compensated temperature response samples of sample bar 50 may be stored in RAM 127. A PROM may be inserted in socket 124 to supply instructions to microprocessor 118 so as to cause it to calculate both:

$$\sum_{o}^{N-1} | T_B(t_i) - T_A(t_i) - Comp | \text{ and: } \frac{T(t_{off} + \Delta)_B - Comp}{T(t_{off} + \Delta)_A}$$

and compare the two figures of merit to threshold values stored in the PROM. If either figure of merit is exceeded "bad" light 40 is lit, while, if neither figure of merit is exceeded, "good" light 38 is lit.

If the microprocessor controller 74 of FIG. 4 is employed, or a hard wired equivalent circuit, authentification device 20 may also be utilized to determine the density, thermal conductivity and heat capacity of a bar of any composition which has the same standard shape as bars 50 or 52. The temperature vs. time response of any sample will have the general S shape shown in FIG. 6. By storing the N compensated temperature responses of an unknown sample in RAM 127 and running an appropriate subroutine located in the PROM in socket 124, the average slope of the temperature response curve and its Y-intercept may be calculated. The weight (w), and volume (v) of the bar whose thermal characteristics are desired may be easily determined and provided as input to microprocessor 118. In this particular embodiment, microprocessor 118 is programmed to calculate and display, on LED digital display 44, the heat capacity of the bar, given by:

$$C_{bar} = A_1/slope \times w,$$

where slope is the average slope of the S curve, w is the weight of the bar, and $A_1$ is an emperically determined constant. Microprocessor 118 is also programmed to calculate and display, on LED digital display 44, the thermal conductivity of the bar, given by:

$$K = \frac{A_2 l^2 P}{W Y_{int}}$$

where $Y_{int}$ is the Y-intercept of the average slope of the S curve, V is the volume of the bar, l is the length of the bar, P is the density of the bar, and $A_2$ is an emperically determined constant. The volume and length of the bar are known due to the geometry of supports 48, bar heater 56 and bar sensor 58. The weight, and therefore the density may be easily determined.

I claim:

1. In a system for determining the thermal characteristics of a sample and for comparing them to the corresponding thermal characteristics of a standard, said system including a heater for applying a heat pulse of finite duration to said sample or said standard and a sensor for measuring the temperature response of said sample or said standard at a plurality of successive instants of time, $t_i$, following the application of said heat pulse, that improvement comprising:

initial temperature compensation means for determining a compensation factor, Comp, representative of the difference, if any, between the temperature of said standard at the time of applying said heat pulse thereto and the temperature of said sample at the time of applying said heat pulse thereto, and means for determining the difference, Diff. $(t_i)$, between said responses according to the formula $$T_A(t_i) - T_B(t_i) - Comp = Diff.(t_i)$$

where $T_A(t_i)$ is the sensed temperature of the standard at a time $t_i$ seconds after said heat pulse is applied thereto and $T_B(t_i)$ is the sensed temperature of the sample $t_i$ seconds after said heat pulse is applied thereto.

2. The system of claim 1 further comprising recording means for recording a plurality of said temperature responses of said standard, $T_A(t_i)$, for $i = 0, 1, 2 \ldots N-1$.

3. The improvement of claim 2 further comprising:
absolute value means for generating N absolute values of said differences at N successive instants of time, $t_i$, for $i = 0, 1, 2, \ldots N-1$, following the application of said heat pulse;
accumulator means for accumulating said N absolute values to yield a figure of merit given by, $$\sum_{o}^{N-1} | T_A(t_i) - T_B(t_i) - Comp | \; ; \text{and}$$

comparator means for comparing said figure of merit to a predetermined value.

4. The improvement of claim 3 further comprising display means, responsive to said comparator, having a first state which is activated when said figure of merit is less than said predetermined value and a second state which is activated when said figure of merit is greater than or equal to said predetermined value.

5. In a system for determining the thermal characteristics of a sample and for comparing them to the corresponding characteristics of a standard, said system including a heater for applying a heat pulse of finite duration to said standard or said sample at one point thereof and monitoring the temperature vs. time response at a second point thereof at a plurality of successive instants of time, $t_i$, that improvement comprising:

a reference sensor for determining the temperature, $T_{amb}$, of the environment adjacent said standard and said sample during the period of time preceeding the application of said heat pulse to said first point of said standard material or said sample material sensor means for sensing the temperature, $\overline{T}(t_i)$ at said second point of said standard or said sample at at least one said instant of time, following the application of said heat pulse, and reference compensating temperature response means for indicating the value $$T(t_i) = \overline{T}(t_i) - T_{amb}$$

for $i \geq 0$, where $T(t_i)$ is the reference compensated temperature of said standard or said sample at successive instants of time, $t_i$.

6. The improvement of claim 5 further comprising means for recording N said reference compensated temperature responses of said standard, $T_A(t_i)$, at N successive instants of time, $t_i$, following the application of said heat pulse.

7. The improvement of claim 6 further comprising subtractor means for determining an ambient temperature compensated difference, $Diff._{amb}(t_i)$ between said reference compensated temperature of said standard, $T_A(t_i)$, and said reference compensated temperature of said sample, $T_B(t_i)$, at said instants of time following the application of said heat pulse, where $Diff._{amb}(t_i)$ is given by:

$$Diff._{amb}(t_i) = T_A(t_i) - T_B(t_i).$$

8. The improvement of claim 7 further comprising:
absolute value means for generating the absolute values of said ambient temperature compensated differences;
accumulator means for accumulating N said absolute values to yield a figure of merit given by $$\sum_{o}^{N-1} | T_A(t_i) - T_B(t_i) | \; ; \text{and}$$

comparator means for comparing said figure of merit to a predetermined threshold.

9. The improvement of claim 8 further comprising display means, responsive to said comparator, and having a first state wherein said figure of merit is less than said predetermined value and a second state wherein said figure of merit is greater than or equal to said predetermined value.

10. The improvement of claim 7 further comprising:

initial temperature compensation means for determining a compensation factor, Comp. = $T_A(O) - T_B(O)$, representative of the difference, if any, between the temperature of said standard at the time of applying said heat pulse thereto, $T_A(O)$, and the temperature of said sample at the time of applying said heat pulse thereto, $T_B(O)$;

means for determining the ambient temperature compensated and initial temperature compensated difference between the temperature of said standard, $T_A(t_i)$, and the temperature of said sample, $T_B(t_i)$, at said successive instants of time, $t_i$, where said ambient temperature compensated and initial temperature compensated difference is given by $T_A(t_i) - T_B(t_i) -$ Comp.

11. The improvement of claim 10 further comprising:
absolute value means for generating the absolute values of said ambient temperature compensated and initial temperature compensated differences;

accumulator means for accumulating N said absolute values to yield a figure of merit given by $$\sum_{o}^{N-1} | T_A(t_i) - T_B(t_i) - Comp. | \text{ ; and}$$

comparator means for comparing said figure of merit to a predetermined threshold.

12. The improvement of claim 11 further comprising display means for physically indicating when said figure of merit is greater than or equal to said predetermined threshold.

13. The improvement of claim 5, 6, 7, 8, 9, 10, 11 or 12 wherein said system comprises a base, a test chamber including said heater mounted on said base, and a fan for circulating air within said test chamber, and wherein said reference sensor is positioned within said base.

14. In the process of determining the thermal characteristics of a material sample in which a heat pulse of finite duration is applied to the sample at a first point and the temperature v. time response of the sample is monitored at a second point spaced from said first point, that improvement wherein:
prior to applying said heat pulse to said sample, the temperature v. time response of said sample at said second point is equilibrated by measuring the rate of change of the temperature at said second point during a first period, and applying said heat pulse only after said rate of change is less than a first predetermined value.

15. The improvement of claim 14 wherein said temperature v. time response is equilibrated by measuring said rate of change during said first period during which an air flow is being directed over said sample, terminating said air flow after said rate of change during said first period has been determined to be less than said first predetermined value, thereafter measuring said rate of change during a second period in which air flow is not being directed over said sample, and applying said heat pulse only after said rate of change during said second period has been determined to be less than a second predetermined value.

16. The improvement of claim 15 wherein said first and second predetermined values are identical.

17. In a system for determining the thermal characteristics of a material sample including a heater for applying a heat pulse of finite duration to the sample at one point and a sensor for monitoring the temperature v. time response of the sample at a second point, that improvement comprising:
a controller arranged to monitor said temperature v. time response and determine an index indicative of the rate of change of said temperature at said second point, and operative to cause said heater to apply said heat pulse only after said index has been determined to be less than a predetermined value.

18. The system of claim 17 including a fan arranged to direct an air flow past said sample when said fan is on, and wherein said controller is arranged
(a) to turn said fan on and determine said index at said second point when said fan is on,
(b) to turn said fan off after said index while said fan is on has decreased to less than a first predetermined value,
(c) after a predetermined period to determine said index at said second point while said fan is off, and
(d) to cause heat pulse to be applied to said first point after said index while said fan is off has been determined to be less than a second predetermined value.

19. In a system for determining the thermal characteristics of a sample and for comparing them to the corresponding thermal characteristics of a standard, said system including a heater for applying a heat pulse of finite duration to a first point of said standard or said sample and a sensor for measuring the temperature response at a second point of said standard or said sample, a non-alloyed gold forgery detector comprising:
control means for activating said heater from time $t=0$ to time $t=t_{off}$ so as to apply said heat pulse to said standard and said sample; and
means for determining the ratio $$\frac{T_B(t_{off} + \Delta)}{T_A(t_{off} + \Delta)}$$

where $T_B(t_{off}+\Delta)$ is the temperature of said second point of said sample at a time $\Delta$ after termination of said heater pulse, $T_A(t_{off}+\Delta)$ is the temperature of said second point of said standard at a time $\Delta$ after termination of said heat pulse, and $\Delta$ is less than one second.

20. The forgery detector of claim 19 further comprising means for determining an initial temperature compensation factor, Comp. = $T_A(O) - T_B(O)$, where $T_A(O)$ and $T_B(O)$ are the temperatures at time $t=o$ of said second point of said standard and said sample respectively, and means for determining the ratio $$\frac{T_B(t_{off} + \Delta) - Comp.}{T_A(t_{off} + \Delta)}$$

21. A system for determining the ratio of density (P) to thermal conductivity (R) of a materials sample comprising:
a heater for applying a heat pulse of finite duration to said sample at a first point,
a sensor for monitoring the temperature of said sample at a second point spaced from said first point,
means for determining the resulting changes of temperature with respect to time of said sample, determining the slope of the temperature v. time curve during a period of time subsequent to the time when said heat pulse is applied to said heater when said slope is substantially constant, and determining the absolute value (Y) of the point of intersection of an extension of the substantially constant slope portion of said curve with the temperature axis, and means for determining said ratio according to the formula $$Y = \frac{Kl^2}{W} \cdot \frac{P}{R}$$

where l is the distance between said first and second points, W is the weight of said sample, and K is a constant.

22. The system of claim 21 including means for determining the heat capacity, C, of said materials sample according to the formula $$dT/dt = A/WC$$

wherein dT/dt is said slope of said temperature v. time curve during said period of time, and A is a constant.

23. In a system for determining the thermal characteristics of a material sample and comparing them to the corresponding characteristics of a standard and including a heater for applying a heat pulse of finite duration to the standard or sample at one point and a sensor for monitoring the resulting temperature v. time response of the standard or sample at a second point, that improvement including:

means for sensing the temperature of said sample before said heat pulse is applied thereto and for applying heat to or removing heat from said sample if said sensed temperature level is different from the temperature of said standard before said heat pulse was applied thereto.

* * * * *